United States Patent
Aizaki et al.

(10) Patent No.: US 8,164,623 B2
(45) Date of Patent: Apr. 24, 2012

(54) MICROSCOPE IMAGE PROCESSING DEVICE AND PROGRAM FOR DETERMINING A TYPE OF AN OPTICAL ELEMENT

(75) Inventors: Shinichiro Aizaki, Tokyo (JP); Yujin Arai, Tokyo (JP)

(73) Assignee: Olympus Corporation, Tokyo (JP)

( * ) Notice: Subject to any disclaimer, the term of this patent is extended or adjusted under 35 U.S.C. 154(b) by 1158 days.

(21) Appl. No.: 12/002,737

(22) Filed: Dec. 18, 2007

(65) Prior Publication Data

US 2008/0151367 A1 Jun. 26, 2008

(30) Foreign Application Priority Data

Dec. 20, 2006 (JP) ................................. 2006-343620

(51) Int. Cl.
- *H04N 7/18* (2006.01)
- *G02B 21/36* (2006.01)
- *G02B 21/06* (2006.01)

(52) U.S. Cl. ............ 348/79; 348/80; 359/385; 359/386; 359/387; 359/389; 359/390

(58) Field of Classification Search .............. 348/79, 348/80; 359/385–390
See application file for complete search history.

(56) References Cited

U.S. PATENT DOCUMENTS

| | | | |
|---|---|---|---|
| 6,051,835 A | 4/2000 | Pettipiece et al. | |
| 6,108,082 A | 8/2000 | Pettipiece et al. | |
| 7,330,268 B2 | 2/2008 | Pettipiece et al. | |
| 2005/0286048 A1* | 12/2005 | Kitagawa | 356/318 |
| 2006/0109546 A1* | 5/2006 | Namba et al. | 359/385 |
| 2006/0237666 A1* | 10/2006 | Kubo | 250/458.1 |

FOREIGN PATENT DOCUMENTS

| | | |
|---|---|---|
| JP | 07-193744 A | 7/1995 |
| JP | 08-338947 A | 12/1996 |
| JP | 2002-196245 A | 7/2002 |
| JP | 2003-126014 A | 5/2003 |
| JP | 2005-164612 A | 6/2005 |

OTHER PUBLICATIONS

Japanese Office Action dated Aug. 2, 2011 (and English translation of relevant parts thereof) in counterpart Japanese Application No. 2006-343620.

* cited by examiner

*Primary Examiner* — Haresh N Patel

(74) *Attorney, Agent, or Firm* — Holtz, Holtz, Goodman & Chick, PC

(57) ABSTRACT

An unit for switchable arranging an arbitrary optical element on an optical path of fluorescence from among a plurality of types of the optical elements that transmit an excitation beam for exciting a sample and fluorescence emitted from the sample; an unit for picking up the observation image via the optical element arranged; and an unit for determining a type of the optical element arranged on the basis of the observation image picked up are prepared in order to provide a microscope image processing device, a program product, a program transmission medium and a method are provided, by which an optical element such as a fluorescence cube set on a fluorescence microscope can be identified on the basis of a detection result of an image pick up device that picks up an image of a sample to be observed by using the fluorescence microscope.

10 Claims, 10 Drawing Sheets

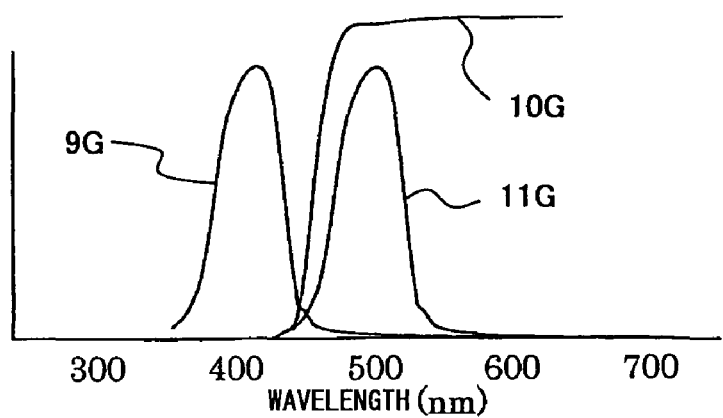
F I G. 5

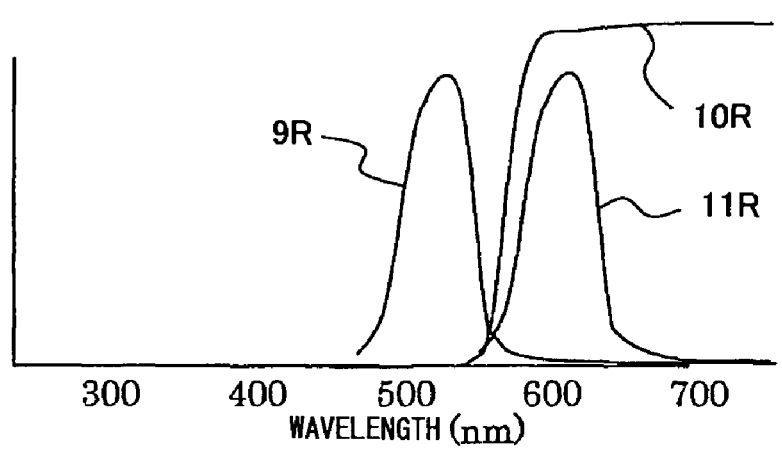
F I G. 6

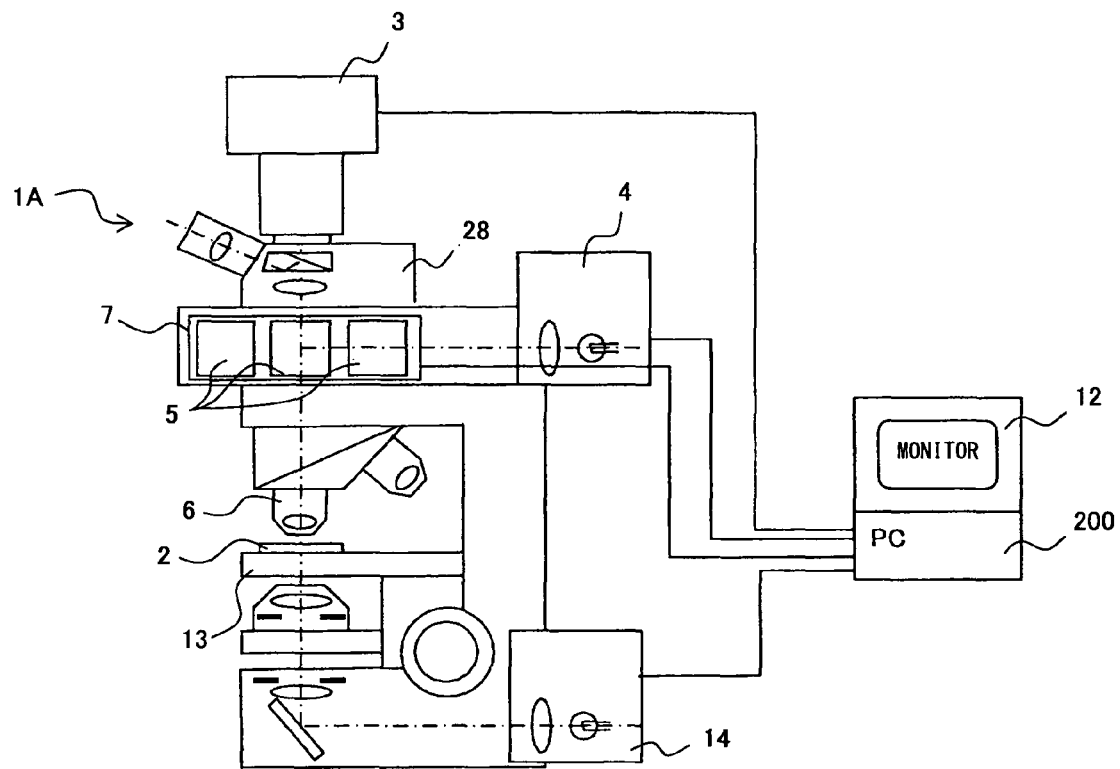
F I G. 7

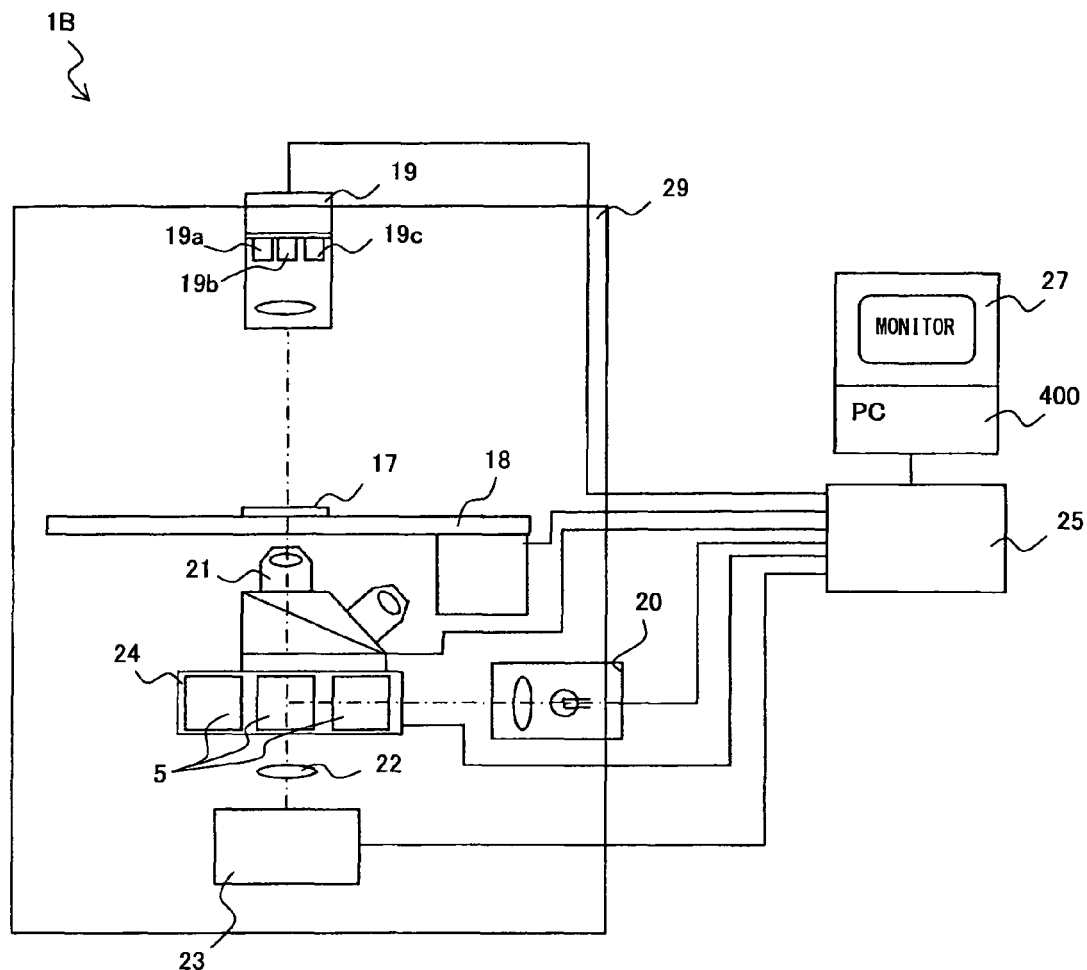
F I G. 9

MICROSCOPE IMAGE PROCESSING DEVICE AND PROGRAM FOR DETERMINING A TYPE OF AN OPTICAL ELEMENT

CROSS REFERENCE TO RELATED APPLICATIONS

This application is based upon and claims the benefit of priority from the prior Japanese Patent Application No. 2006-343620, filed on Dec. 20, 2006, the entire contents of which are incorporated herein by reference.

BACKGROUND OF THE INVENTION

1. Field of the Invention

The present invention relates to a microscope image processing device that includes a fluorescence microscope and an image pick up device in a combined manner, a microscope image processing program, and a microscope image processing method, and particularly to a microscope image processing device, a microscope image processing program product, a microscope image processing program transmission medium, and a microscope image processing method, by which types of a fluorescence cube on an optical path can be determined.

2. Description of the Related Art

In the conventional fluorescence microscope, a light beam of a particular wavelength bandwidth is emitted onto the sample for the excitation, and the fluorescence emitted from the sample is used for the observation. In this type of the fluorescence microscope, for the observation, a fluorescence cube that is the most suitable with respect to the type of the sample or the fluorescence dye is selected from among a plurality of fluorescence cubes (fluorescence dye) mounted on the turret in order to come to be set on the optical path.

FIG. 1 shows a conventional fluorescence microscope image pick up system.

In FIG. 1, a fluorescence microscope 1 comprises objective lenses 6, fluorescence cubes 5, an epi-illumination light source 4, an optical column 28, and an image pick up device 3, so that visual observation of a sample set on the stage (sample stage) 13 can be made and also that the image of the sample can be guided along an observation optical path a1 to an external environment. The image pick up device 3 is set on the plane, on the observation optical path a1, on which the observation image coming out from the fluorescence microscope 1 is projected.

In this fluorescence microscope 1, an illumination beam emitted from the epi-illumination light source 4 such as a mercury lamp is reflected by the fluorescence cube 5, and is cast onto the sample 2 via the objective lens 6. A plurality of fluorescence cubes 5 are mounted on the turret 7, and the operator of the fluorescence microscope 1 can replace the fluorescence cubes 5 to be set on the optical path also that the most suitable combination between the fluorescence cube 5 and the fluorescence dye of the sample is achieved.

And, the operator can cause a monitor device 12 to display the observation image picked up by the image pick up device 3.

FIG. 2 shows an example of the fluorescence cube 5.

As shown in FIG. 2, the fluorescence cube 5 comprises a band pass filter 9, a dichroic mirror 10, and an absorption filter 11, and some of the fluorescence cubes 5 are used in a combination that is the most suitable for the fluorescence dye of the sample 2. The number of the fluorescence cubes 5 that can be mounted on the fluorescence microscope 1 is limited, thus the operator of the fluorescence microscope 1 appropriately replaces them in order to attain the best combination between the fluorescence cubes 5 and the fluorescence dye.

It sometimes occurs that the operator cannot remember which types of the fluorescence cubes were set at which positions on the turret 7 after they replaced the fluorescence cubes 5. In such a case, time and labor is taken in order to find the target fluorescence cube 5. In the case of the observations using the fluorescence microscopes especially, when the sample 2 is kept being irradiated with the illumination beam for a long time, the discoloration of the fluorescence dye occurs, which affects the observation.

In order to avoid such a problem, in some microscopes, names of the fluorescence cubes 5 can be described on the turret 7. However, to change names of the fluorescence cubes 5 when the operator replaces the fluorescence cubes 5 is not an essential operation for the operator, so that he or she often forgets to change the names of the fluorescence cubes 5.

As a technique for solving this problem, there is a technique as disclosed in, for example, Japanese Patent Publication No. 8-338947. In this technique, a display portion is provided on the outer surface of the fluorescence cube 5, and the front surface of the turret 7 for holding the fluorescence cubes 5 has a plurality of openings for exposing to the external environment the display portions of the fluorescence cubes 5 at all the replacement positions at which the fluorescence cubes 5 can be, so that all the display portions can be viewed from the external environment through the plurality of openings.

SUMMARY OF THE INVENTION

According to one aspect of the present invention, a microscope image processing device of the present invention comprises:

an optical element switching unit for switchably arranging an arbitrary optical element on an optical path of fluorescence from among a plurality of types of the optical elements that transmit an excitation beam for exciting a sample and fluorescence emitted from the sample;

an image pick up unit for picking up the observation image via the optical element arranged by the optical element switching unit; and an optical element determination unit for determining a type of the optical element arranged by the optical element switching unit on the basis of the observation image picked up by the image pick up unit.

BRIEF DESCRIPTION OF THE DRAWINGS

The present invention will be more apparent from the following detailed description when the accompanying drawings are referenced.

FIG. 5 shows spectral characteristics of the green color component of a band pass filter 9G, a dichroic mirror 10G, and an absorption filter 11G;

FIG. 6 shows spectral characteristics of the red color component of a band pass filter 9R, a dichroic mirror 10R, and an absorption filter 11R;

FIG. 7 shows a fluorescence microscope image pick up system to which a second embodiment of the present invention is applied;

FIG. 9 shows a fluorescence microscope image pick up system to which a third embodiment of the present invention is applied.

DESCRIPTION OF THE PREFERRED EMBODIMENTS

Figure 1:
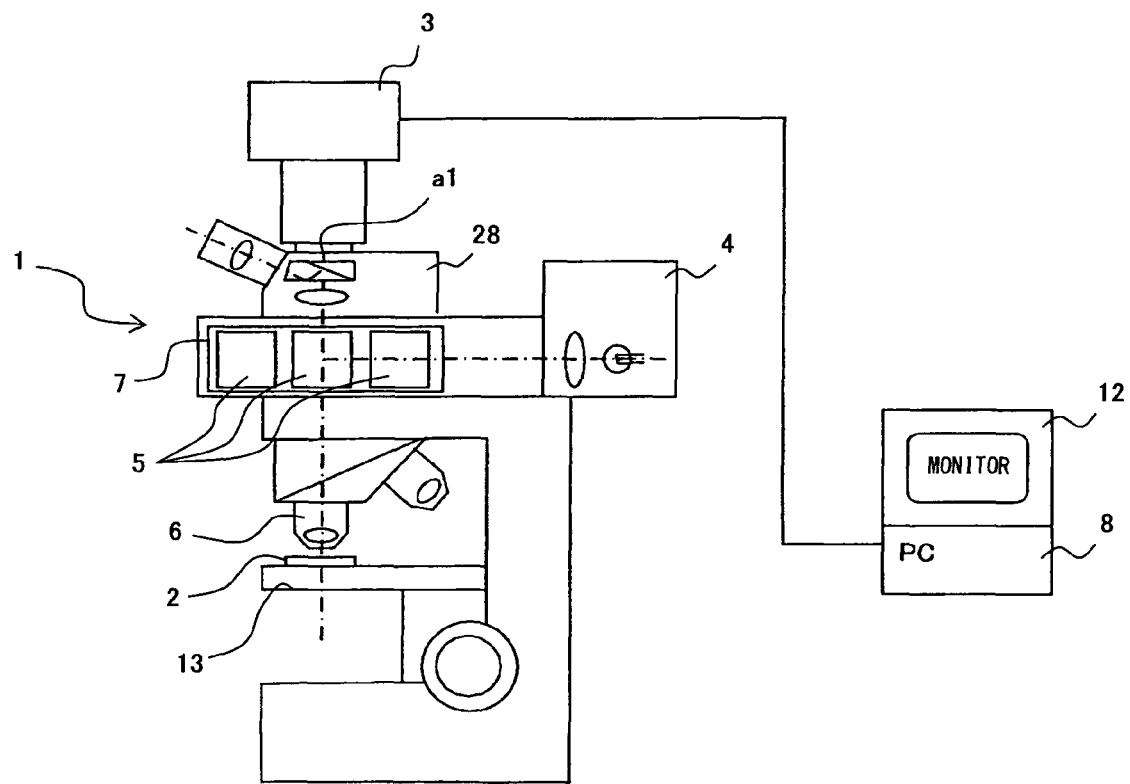
FIG. 1 shows a conventional fluorescence microscope image pick up system.

Hereinafter, the embodiments of the present invention will be explained by referring to the drawings.

First Embodiment

Figure 3:
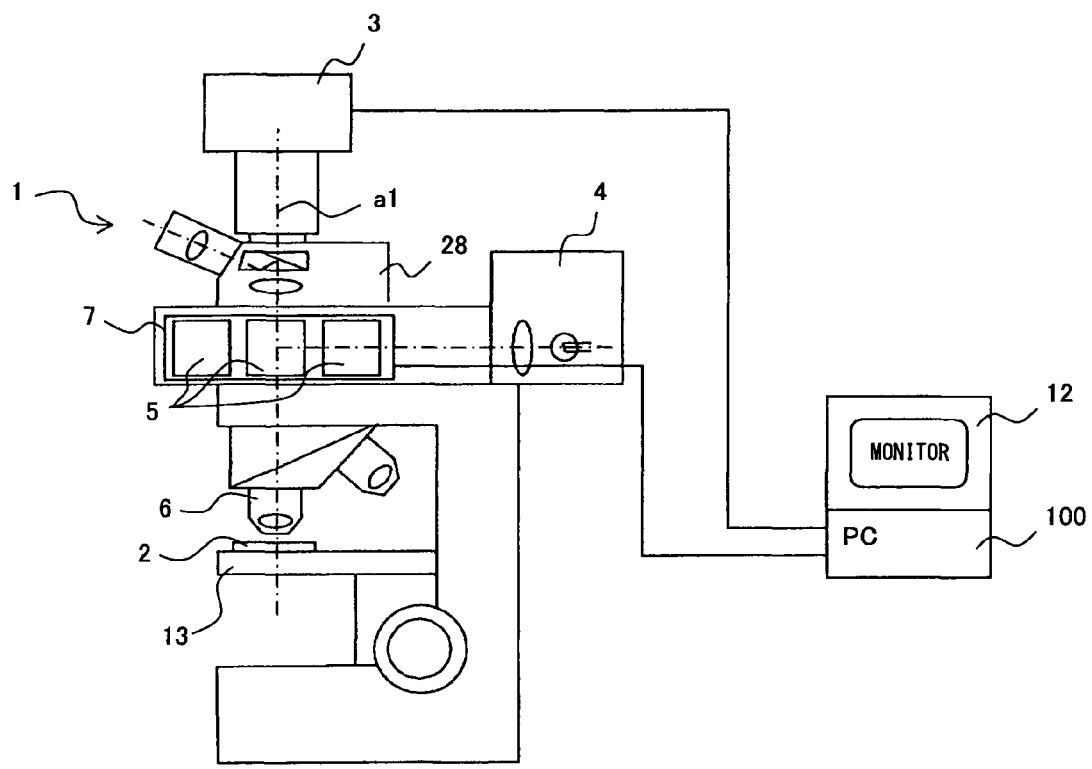
FIG. 3 shows a fluorescence microscope image pick up system to which a first embodiment of the present invention is applied.

FIG. 3 shows a fluorescence microscope image pick up system to which a first embodiment of the present invention is applied.

In FIG. 3, the fluorescence microscope 1 comprises the objective lenses 6, the fluorescence cubes 5, the epi-illumination light source 4, the optical column 28, the image pick up device 3, so that visual observation of a sample set on the stage (sample stage) 13 can be made and also that the image of the sample can be guided along an observation optical path a1 to the external environment. The image pick up device 3 such as a color image pick up device or the like is set on the plane, on the observation optical path a1, on which the observation image coming out from the fluorescence microscope 1 is projected.

In this fluorescence microscope 1, an illumination beam emitted from the epi-illumination light source 4 such as a mercury lamp is reflected by the fluorescence cube 5, and is cast onto the sample 2 via the objective lens 6. A plurality of fluorescence cubes 5 are mounted on the turret 7, and the operator of the fluorescence microscope 1 can replace the fluorescence cubes 5 to be set on the optical path also that the most suitable combination between the fluorescence cube 5 and the sample is set on the optical path a1.

Then, the operator can control the turret 7 via a PC 100 such as a personal computer or the like while causing the monitor 12 to display the observation images picked up by using the image pick up device 3.

Figure 2:
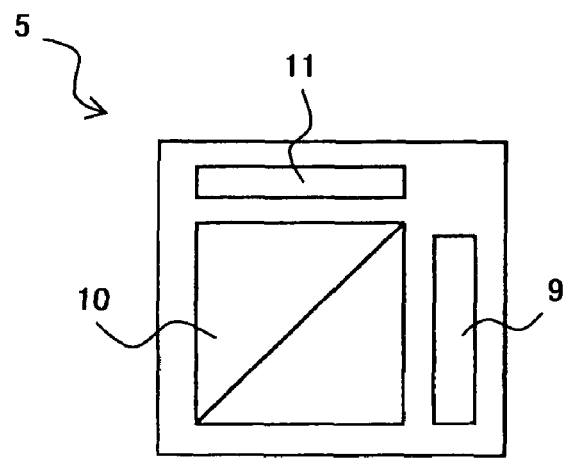
FIG. 2 shows an example of a fluorescence cube 5.

In the first embodiment of the present invention, a case is assumed in which three types of the fluorescence cubes 5 such as, for example, the ones shown in FIG. 2 are used.

Figure 4:
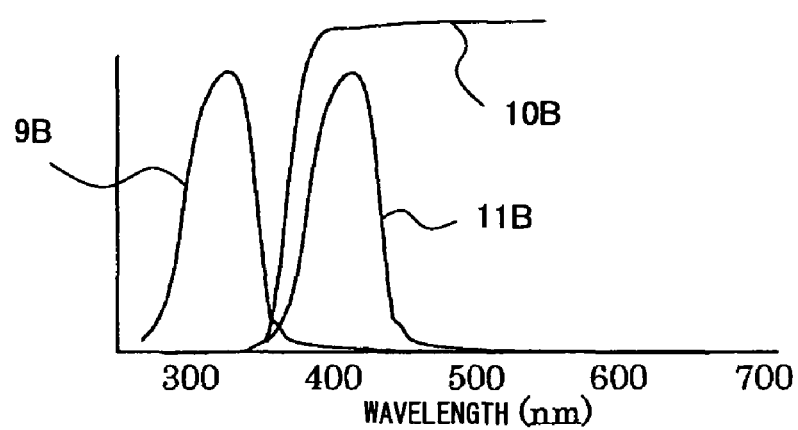
FIG. 4 shows spectral characteristics of the blue color component of a band pass filter 9B, a dichroic mirror 10B, and an absorption filter 11B.

FIG. 4 shows the spectral characteristics of the blue color component of a band pass filter 9B, a dichroic mirror 10B, and an absorption filter 11B. FIG. 5 shows the spectral characteristics of the green color component of a band pass filter 9G, a dichroic mirror 10G, and an absorption filter 11G. FIG. 6 shows the spectral characteristics of the red color component of a band pass filter 9R, a dichroic mirror 10R, and an absorption filter 11R.

In FIG. 3, only the particular wavelength components in the beam emitted from the epi-illumination light source 4 are transmitted through the band pass filter 9, reflected by the dichroic mirror 10, and cast onto the sample 2 through the objective lens 6. The sample 2 emits fluorescence generated by the excitation due to the beam cast on the sample 2. This fluorescence passes through the objective lens 6, and is transmitted through the dichroic mirror 10 and the absorption filter 11. Thereafter, the image formed by this fluorescence is picked up by the image pick up device 3, and the picked up image is taken into the PC 100 in order to be displayed on the monitor device 12.

Because many fluorescence dyes are used for the observation of the sample 2 in the fluorescence microscope 1, only the fluorescence cubes 5 mounted on the turret 7 can not cope with the variety of the fluorescence dyes. Accordingly, it is necessary to alter the combination of the fluorescence cubes 5 to be mounted on the turret 7 so that they correspond to the fluorescence dye. Because of this necessity, the initial operations are performed on the microscope image pick up system installed on the PC 100. The initial operations will be explained hereinafter.

First, the turret 7 is revolved after the activation of the microscope image pick up system, and an image is obtained for each of the fluorescence cubes 5. At that time, the pick up is performed by the image pick up device 3 by using light such as the auto fluorescence of the objective lens caused by the epi-illumination light from the epi-illumination light source 4 or the external light via the dichroic mirror 10 and the absorption filter 11 in the fluorescence cube 5. Also, when the sample 2 is set on the stage 13, the fluorescence itself coming from the sample 2 is detected.

The beams picked up by the image pick up device 3 are beams that are transmitted through the absorption filters 11B, G, and R shown in FIGS. 4, 5, and 6, accordingly, the obtained images have the special characteristics that depend on the color components for each of the fluorescence cubes 5. For example, the special characteristic of the fluorescence cube 5 whose spectral characteristic is shown in FIG. 4 is the blue color component that has the wavelength raging from 430 nm through 480 nm, the special characteristic of the fluorescence cube 5 whose spectral characteristic is shown in FIG. 5 is the green color component that has the wavelength ranging from 500 nm through 570 nm, and the special characteristic of the fluorescence cube 5 whose spectral characteristic is shown in FIG. 6 is the red color component that has the wavelength ranging from 610 nm through 780 nm.

The PC 100 detects the color components of the image for each of the fluorescence cubes 5, and displays the detection result on a turret control section on the monitor 12.

After performing the initialization as described above, the operator performs the observations by using the fluorescence microscope 1 and obtains images by using the microscope image pick up system via the turret control section on the monitor device 12 and the image pick up device control unit.

Also, the fluorescence cubes 5 mounted on the turret 7 are selected by the operator of the fluorescence microscope 1 in accordance with the purposes. In the microscope image pick up system installed on the PC 100, the types of the fluorescence cubes 5 can be determined on the basis of the transmitted beams such as beams in blue, green, and red.

(Variation 1 of the First Embodiment)

In the fluorescence microscope image pick up system, the images picked up respectively with a plurality of fluorescence cubes 5 are sometimes displayed in an overlapped state. Accordingly, a false color is set in accordance with the above determined fluorescence cube 5. The images picked up with the respective fluorescence cubes 5 are displayed with the set false color for overlapping.

In the setting of the false color, when, for example, an image of a fluorescence sample is picked up by using a color image pick up element through a red fluorescence cube, the obtained image data includes not only the R components, but also the G components, and in some conditions the B components too. Similarly, when the blue fluorescence cube is used, the R and G components can be included, and when the green fluorescence cube is used, the R and B components can be included. Accordingly, when the images of these three types are just overlapped, the R, G, and B components are mixed. In order to avoid this overlapping, the images of the R, G, and B components are respectively converted into pieces of intensity information prior to the overlapping of the images, thereby the overlapping is performed for each of the three types of the components. In this case, the images are processed so that each image only includes one of the R, G, B components for avoiding the mixture. However, when a particular color is desired to be expressed, the R, G, and B components may be multiplied by a coefficient that represents a certain ratio.

(Variation 2 of the First Embodiment)

In the above described first embodiment, the turret 7 is controlled by the PC 100, however, it is also possible to manually control the turret 7.

Second Embodiment

FIG. 7 shows a fluorescence microscope image pick up system to which a second embodiment of the present invention is applied.

The configuration of the second embodiment is obtained by adding to the first embodiment a transparent illumination light source 14. In this second embodiment, the transparent illumination light source 14 is turned on when a fluorescence microscope 1A is initialized upon the activation. The illumination light emitted from the transparent illumination light source 14 travels through the objective lens 6 and the fluorescence cube 5 in order to be used for the pick up of images performed by the image pick up device 3.

Then, the microscope image pickup system installed on a PC 200 determines the fluorescence cube 5 by picking up images for each of the fluorescence cubes 5 and detecting the colors of the images.

(Variation 1 of the Second Embodiment)

Figure 8:
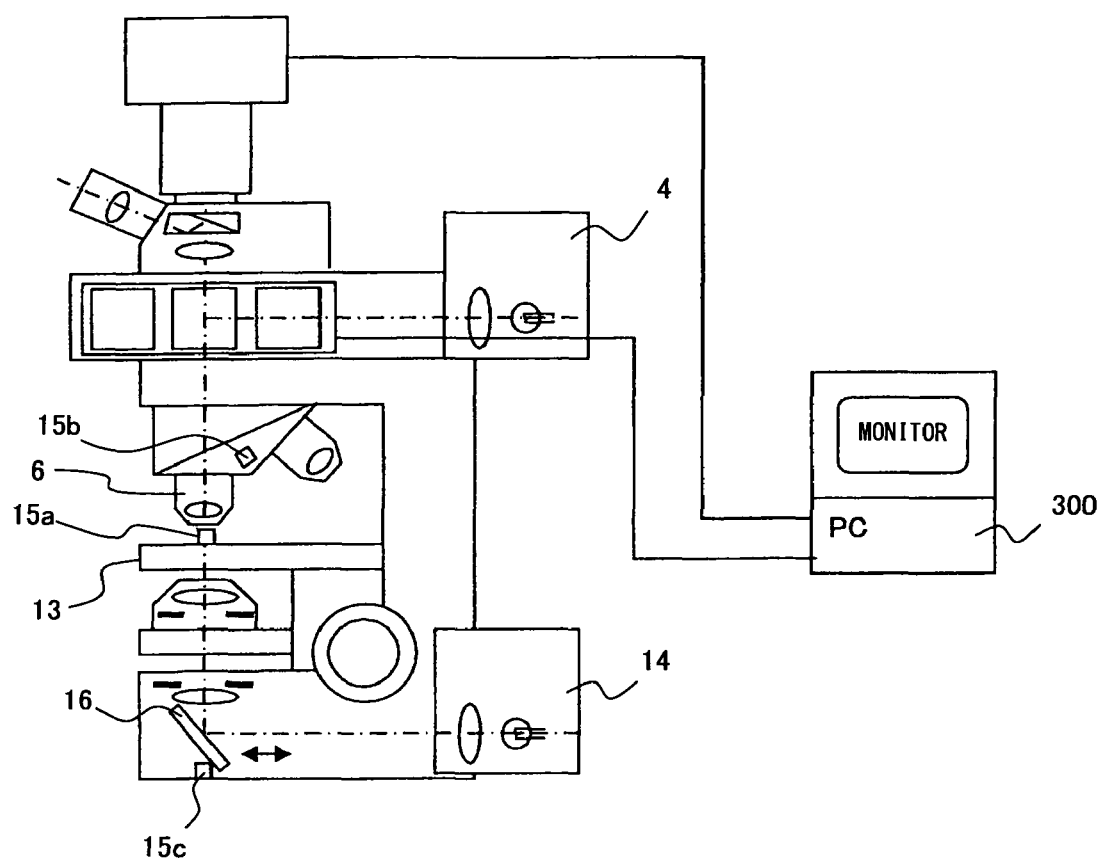
FIG. 8 shows a fluorescence microscope image pick up system to which a first variation of the second embodiment of the present invention is applied.

FIG. 8 shows a fluorescence microscope image pick up system to which a first variation of the second embodiment of the present invention is applied.

As shown in FIG. 8, one of auxiliary light sources 15 is selected and set on the optical axis.

For example, an auxiliary light source 15a is detachably set on the stage 13, or an auxiliary light source 15b is set between the objective lenses 6 on the revolver and the revolver is moved to the position of the auxiliary light source 15b upon the initialization.

It is also possible to employ a configuration in which a mirror 16 is configured to be movable and an auxiliary light source 15c is set below the mirror 16.

By employing the above configuration, it is possible to attain the same effect as in the second embodiment.

(Variation 2 of the Second Embodiment)

A memory device included in a PC 300 such as a personal computer or the like that has installed a microscope image pick up system thereon stores the spectral characteristics of the transparent illumination light source 14 or the auxiliary light sources 15, the spectral sensitivity of the image pick up device 3, and the spectral characteristics of a plurality of the fluorescence cubes 5 in order to hold a measurement value of the image picked up for each fluorescence cube 5 by using the image pick up device 3. And, the image data obtained for each fluorescence cube 5 and the measurement value is compared to each other when initiating, thereby it is presumed which of the fluorescence cube 5 is used.

According to this variation 2 of the present invention, it is possible to identify the types of the fluorescence cubes 5.

(Variation 3 of the Second Embodiment)

This variation 3 of the second embodiment includes, in addition to the configuration of the variation 2, a configuration in which the spectral characteristics of the fluorescence dye of the sample being observed can be input to a PC 300. The color of the fluorescence itself is obtained by the calculations of the spectral characteristics of the input spectral characteristics of the fluorescence dye, and the obtained color is set as the false color corresponding to the fluorescence cube 5.

According to this variation 2, it is possible to set the false color that greatly matches the color of the fluorescence.

Third Embodiment

FIG. 9 shows a fluorescence microscope image pick up system to which a third embodiment of the present invention is applied.

In FIG. 9, an inverted microscope 1B comprises a stage (sample stage) 18 that is for mounting the sample 17 and that is movable in the X, Y, and Z directions, a transparent illumination light source 19 for performing the transparent illumination on the sample 17, an epi-illumination light source 20 for performing the epi-illumination onto the sample 17, objective lenses 21 for collecting light from the sample 17, an imaging lens 22, and an image pick up device 23 for picking up images formed by the imaging lens 22.

The image pick up device 23 is constituted of, for example, a cold monochrome CCD camera.

The operator operates a PC 400 such as a personal computer. By a controller 25 that operates in accordance with the instructions given by a microscope image pick up system installed on the PC 400 (that has a monitor device 27), the stage 18, the transparent illumination light source 19, the epi-illumination light source 20, an objective lens revolver mounting a plurality of objective lenses 21, the image pick up device 23, and a turret 24 are controlled.

Also, the main body of the inverted microscope 1B is stored in a dark box 29 so that external light does not influence the optical path.

A plurality of fluorescence cubes 5 for reflecting the illumination light from the epi-illumination light source 20 are mounted on the turret 24 similarly to the above embodiments.

Also, the transparent illumination light source 19 includes at least three monochromatic light sources 19a, 19b, and 19c respectively for emitting beams different in color.

Figure 10:
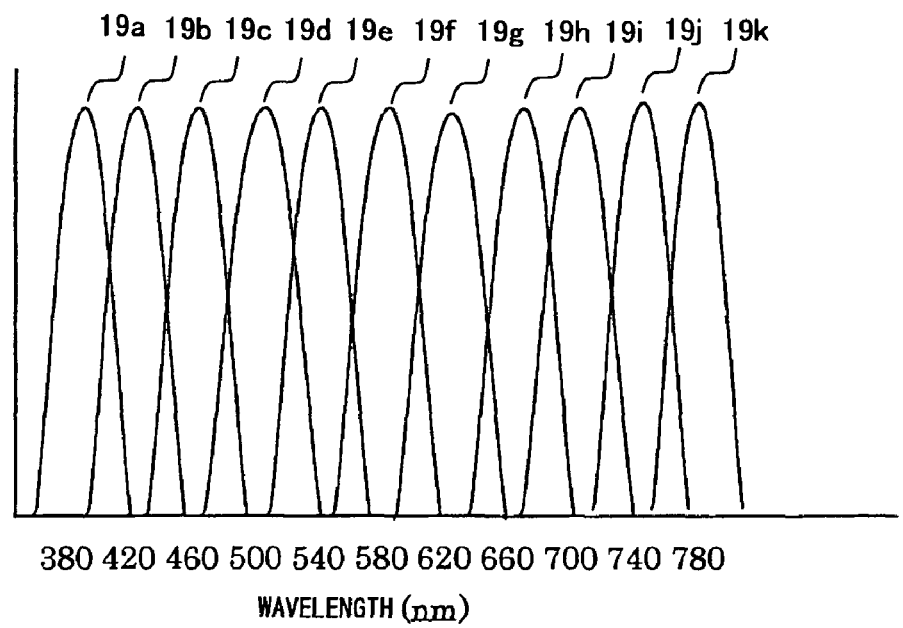
FIG. 10 shows an example of the spectral characteristic of the transparent illumination light source 19.

FIG. 10 shows an example of the spectral characteristic of the transparent illumination light source 19.

The transparent illumination light source 19 includes eleven types of LEDs (transparent light sources 19a through 19k) having the spectral characteristics as shown in, for example, FIG. 10.

Similarly to the fluorescence cube 5 on the above described turret 7, the fluorescence cubes 5 on the turret 24 in this third embodiment can be replaced for different combinations as necessary.

The operator of the microscope image pick up system according to the third embodiment of the present invention selects the fluorescence cube 5, determines the positions of the sample 17, obtains correct focus on the sample 17, selects the objective lens 21, selects the illumination light, and etc. in order to obtain images of the sample 17.

In the third embodiment of the present invention, the LEDs 19a through 19k of the transparent illumination light source 19 are sequentially caused to emit beams in the respective colors for each of the fluorescence cubes 5 in order to obtain the respective images. Thereafter, the pieces of image data corresponding to the respective colors are compared to one another in order to estimate the character of the absorption filter 11.

Also, similarly to the above first and second embodiments, it is possible to determine the types of the fluorescence cubes 5, and the determination result is displayed on the control window displayed on the monitor device 27 in the PC 400. Also, similarly to the first and second embodiments, the false color is set for each of the fluorescence cubes 5.

Further, in this third embodiment of the present invention, the turret 24 has a blank portion in which a fluorescence cube 5 is not placed. It is also possible to perform the transparent illumination observation of the sample 17 by setting the turret 24 so that this blank portion is used.

When a live image observation is to be performed, the three types of the eleven LEDs (light sources 19a through 19k) i.e., the red LED (that is of 620 nm and denoted by 19g), the green LED (that is of 540 nm and denoted by 19e), and a blue LED (that is of 460 nm and denoted by 19c) are sequentially caused to emit light in order to obtain the respective images. Then, the three images are synthesized in order to be displayed on the monitor device 27. Thereby, it is possible to obtain color live images with the maximum update term of the frame.

Also, when still images are to be obtained, the eleven types of LEDs (transparent light sources 19a through 19k) are sequentially caused to emit light in order to obtain the images. In this case, the eleven images correspond to the multi-spectral images of the respective wavelengths. From these multi-spectral images, the spectral image of the sample 17 can be obtained, and an image that precisely reproduces the color of the sample 17 can be obtained.

Also, when the respective colors are different from one another in the shading, the shading images for the respective colors are obtained upon the initialization, and the shading correlation is performed for each color when synthesizing the live images or the still images, thereby, still better images can be obtained.

Also, in the third embodiment of the present invention, the number of the types of the transparent illumination light source 19 is eleven in the visible range, however, it is possible to increase the number of the types of the light sources or to use light sources that emits light in the ultraviolet rays or the infrared rays, thereby the responses from the sample 17 when receiving various wavelengths can be observed.

Also, in the microscope image pick up system according to the third embodiment of the present invention, the optical path is entirely included in the dark box 29, and a cold monochrome CCD camera is used as the image pick up device 23, accordingly by turning off the transparent illumination light source 19 and the epi-illumination light source 20, the weak light such as the bioluminescence can be detected.

The respective embodiments of the present invention have been explained by referring to the drawings. However, the microscope image processing device to which the present invention is applied is not limited to any of the above embodiments as long as the same functions as in the embodiments are realized, and can be a single device, a system or a comprehensive device consisting of a plurality of devices, or a system in which processes are performed via networks such as a LAN, WAN, or the like.

Also, the microscope image processing device to which the present invention is applied can be realized by a system including a CPU, a memory device such as ROM, or RAM, an input device, an output device, an external storage device, a medium driving device, a transportable storage device, and a network connection device in a state in which they are connected to a bus. In other words, the microscope image processing device to which the present invention is applied can be realized by providing a microscope image processing device with a memory device such as ROM or RAM, an external storage device, and a transportable storage medium storing a program code for software that realizes the systems described in the above respective embodiments, and by causing a computer of the microscope image processing device to read the program code in order to execute the read program code.

In this case, the program code itself read from the transportable storage medium or the like realizes the novel functions of the present invention, and transportable storage medium or the like storing that program code is a component that constitutes the present invention.

Examples of the transportable storage medium for providing the program code are a flexible disk, a hard disk, an optical disk, a magneto-optical disk, a CD-ROM device, a CD-R, a DVD-ROM device, a DVD-RAM device, magnetic tape, a non-volatile memory card, a ROM card, and various storage media storing information via a network connection device for the E-mail or computer communication, or the like (in other words, communication lines).

Also, a computer that executes a program code read onto a memory device can realize the functions described in the above respective embodiments, and also an OS that operates on a computer on the basis of the instruction given by that program code can realize the functions described in the above respective embodiments by executing a part or the whole of the processes of the present invention.

Further, the functions described in the above embodiments can be realized by a configuration in which a program (data) read from a transportable storage medium or a program (data) provided by a program (data) provider is written to a memory device included in an expansion board inserted into a computer or an expansion unit connected to a computer, and the CPU or the like included in the expansion board or the expansion unit performs a part or the whole of the processes in accordance with the instructions written as the program code.

In other words, the scope of the present invention is not limited to any of the above described embodiments, and the present invention can take various configurations or shapes without departing from the spirit of the present invention.

What is claimed is:

1. A microscope image processing device for processing an observation image comprising:
    an optical element switching unit which switchably arranges an arbitrary optical element on an optical path of fluorescence from among a plurality of types of optical elements that transmit an excitation beam for exciting a sample and fluorescence emitted from the sample;
    an image pick up device which picks up the observation image via the optical element arranged by the optical element switching unit;
    an optical element determination unit which determines a type of the optical element arranged by the optical element switching unit based on the observation image picked up by the image pick up device;
    an optical element information storage unit which stores information on the plurality of types of optical elements that transmit an excitation beam for exciting the sample and fluorescence emitted from the sample;

an optical element identification unit which identifies the type of the optical element determined by the optical element determination unit by referring to the optical element information storage unit;

a fluorescence dye information storage unit which stores information on a plurality of fluorescence dyes;

a fluorescence dye recognition information input unit which inputs fluorescence dye recognition information for recognizing a fluorescence dye;

a fluorescence dye identification unit which identifies the fluorescence dye whose fluorescence dye recognition information is input by the fluorescence dye recognition information input unit by referring to the fluorescence dye information storage unit; and a false color setting unit which sets a false color on the observation image picked up by the image pick up device based on the type of the optical element determined by the optical element determination unit and based on a fluorescence dye characteristic corresponding to the fluorescence dye identified by the fluorescence dye identification unit.

2. The microscope image processing device according to claim 1, further comprising:

an illumination light source which illuminates the sample, wherein the image pick up device picks up the observation image of the sample illuminated by the illumination light source.

3. The microscope image processing device according to claim 2, wherein the illumination light source includes at least three monochromatic light sources respectively having different wavelengths.

4. The microscope image processing device according to claim 3, wherein the image pick up device picks up a spectral image of the sample illuminated by the respective monochromatic light sources.

5. The microscope image processing device according to claim 1, wherein the image pick up device is a color image pick up device for picking up the observation image in full color.

6. A non-transitory computer-readable storage medium having stored thereon a microscope image processing program for processing an observation image and for controlling a computer to perform functions comprising:

switchably arranging an arbitrary optical element on an optical path of fluorescence from among a plurality of types of optical elements that transmit an excitation beam for exciting a sample and fluorescence emitted from the sample;

picking up the observation image via the switchably arranged arbitrary optical element;

determining a type of the switchably arranged arbitrary optical element based on the picked up observation image;

identifying the determined type of the optical element by referring to stored information on the plurality of types of optical elements that transmit an excitation beam for exciting the sample and fluorescence emitted from the sample;

inputting fluorescence dye recognition information for recognizing a fluorescence dye;

identifying the fluorescence dye whose fluorescence dye recognition information is input by referring to stored information on a plurality of fluorescence dyes; and setting a false color on the picked up observation image based on the determined type of the optical element and based on a fluorescence dye characteristic corresponding to the identified fluorescence dye.

7. The non-transitory computer-readable storage medium according to claim 6, wherein the microscope image processing program further controls the computer to perform functions comprising:

illuminating the sample by an illumination light source; and picking up the observation image of the sample illuminated by the illumination light source.

8. The non-transitory computer-readable storage medium according to claim 7, wherein the illumination light source includes at least three monochromatic light sources respectively having different wavelengths.

9. The non-transitory computer-readable storage medium according to claim 8, wherein the microscope image processing program further controls the computer to perform a function comprising picking up a spectral image of the sample illuminated by the respective monochromatic light sources.

10. The non-transitory computer-readable storage medium according to claim 6, wherein the picked up observation image is in full color.

* * * * *